United States Patent [19]
Lynd et al.

[11] Patent Number: 5,105,475
[45] Date of Patent: Apr. 21, 1992

[54] HEADGEAR WITH EYEGLASS

[75] Inventors: Larry G. Lynd, Canal Winchester; James Hampshire, Solon, both of Ohio

[73] Assignee: Countryside Products Co., Columbus, Ohio

[21] Appl. No.: 754,173

[22] Filed: Aug. 26, 1991

Related U.S. Application Data

[63] Continuation of Ser. No. 555,161, Jul. 20, 1990, abandoned.

[51] Int. Cl.⁵ .............................................. A61F 9/00
[52] U.S. Cl. ............................................. 2/10; 2/12; 2/452; 2/453
[58] Field of Search .............. 2/10, 11, 12, 13, 185 R, 2/199, 452, 453, DIG. 6, DIG. 11

[56] References Cited

U.S. PATENT DOCUMENTS

| | | | |
|---|---|---|---|
| 1,133,056 | 3/1915 | Pachner | 2/10 |
| 1,170,462 | 2/1916 | Schroeder | 2/10 |
| 1,216,635 | 2/1917 | Washington | 2/10 |
| 1,781,832 | 11/1930 | Crenshaw | 2/10 |
| 2,179,719 | 11/1939 | Goskey | 2/10 |
| 4,179,753 | 12/1979 | Aronberg et al. | 2/10 |
| 4,393,519 | 7/1983 | Nicastro | 2/12 |
| 4,630,317 | 12/1986 | Brown et al. | 2/12 |
| 4,712,254 | 12/1987 | Daigle | 2/452 |
| 4,724,546 | 2/1988 | Cumbie, Jr. | 2/12 |
| 4,811,430 | 3/1989 | Janusz | 2/452 |
| 4,815,838 | 3/1989 | Liataud | 2/12 |
| 4,819,274 | 4/1989 | Day | 2/10 |

FOREIGN PATENT DOCUMENTS

| | | | |
|---|---|---|---|
| 57205 | 1/1940 | Denmark | 2/10 |
| 2913059 | 10/1980 | Fed. Rep. of Germany | 2/424 |
| 8601694 | 3/1986 | PCT Int'l Appl. | 2/424 |
| 14855 | 9/1916 | United Kingdom | 2/10 |

Primary Examiner—Werner H. Schroeder
Assistant Examiner—Michael A. Neas
Attorney, Agent, or Firm—Biebel & French

[57] ABSTRACT

Headgear is provided having a head element adapted to be worn by a person and including in combination an eye shield carried by the head element and which may be selectively positioned with respect to the head element in either a shielding or covering position relative to the wearer's eyes or in a stored position. The head element has a section that is positionable on a wearer's forehead in secured relationship by a headband and is formed with a forwardly projecting visor and a storage compartment to contain the eye shield. The storage compartment is formed by spaced apart, rigid walls that are interconnected at their upper ends by a top wall with the bottom of the compartment being open to permit movement of the eye shield into and out of the compartment. The eye shield has a lens structure formed of a generally planar sheet of optically transparent plastic material and is of a configuration to extend across the wearer's eyes terminating in rearwardly extending support arms that pivotally interconnect with the head element whereby the eye shield's lens structure may be swung between a stored position in the compartment and an operative position in front of the wearer's eyes. A detent mechanism is incorporated in the structure to hold the eye shield in a selected position on the head element and out of contacting engagement with the wearer's nose.

19 Claims, 5 Drawing Sheets

HEADGEAR WITH EYEGLASS

This is a continuation of co-pending application Ser. No. 07/555,161 filed July 20, 1990, now abandoned.

FIELD OF THE INVENTION

This invention relates in general to headgear adapted to be worn by a person and incorporating in a combined structure an eyeglass or eye shielding element. It relates more particularly to headgear having a headband adapted to encircle and be removably secured on a person's head and including a storage compartment in which an eyeglass or lens structure is adapted to be stored and from which the eyeglass may be selectively displaced and positioned in operative relationship to the wearer's eyes.

BACKGROUND OF THE INVENTION

Persons who are engaged in outdoor activities invariably find that they need protection from the sun. This need for protection is most notable with respect to the person's eyes since exposure to the sun over prolonged periods of time will not only produce physical strain, but can result in impairment of vision and damage to the person's vision system. One commonly used device to alleviate this problem is a hat or cap or other type of head covering device which includes a forwardly projecting visor, bill or brim which extends a distance forwardly from the person's forehead and provides a shade producing element that tends to reduce the likelihood of the sun's rays being directly incident to the eyes of a person wearing such protective headgear. A second commonly used device to provide protection for the eyes is the sunglass or other protective lens structure having characteristics such that it will attenuate or minimize the effect of the most damaging components of the lightwaves such as those within the ultraviolet spectrum. The sunglasses that are generally worn for eye protection of this type are usually not of an optical type such as in the nature of prescription type glasses and are designed primarily for the sole purpose of attenuating the lightwaves that would be incident on the person's eyes and to thereby minimize the physical eyestrain as well as possible damage. Sunglasses for this purpose also are available in many styles and configurations with the different types ranging from separate eyepieces that are maintained in association by a frame structure with each eyepiece positioned in front of a respective eye, to those which consist of a molded sheet of plastic material that is of a continuous nature, or wraparound style extending across the front of the wearer's face and covering the eye section. These glasses also are of a type wherein the frame or an integral part of the lens structure incorporates or is formed with frame elements that extend along the side of the wearer's head and are adapted to engage with the ears and to thereby in cooperation support the front lens structure on the wearer's nose maintain the glasses in an operative position on the person's head. It is also not uncommon for a person to wear both types of protection, namely the headgear with the sunlight blocking visor as well as a sunglass structure which will cooperatively function to block and to attenuate lightwaves that will be incident to a person's eyes.

While the headgear and eyeglass combinations are capable of performing their respective functions, there are some disadvantages due to the fact that the eyeglasses are uncomfortable to wear and they also present a problem in keeping them readily available It is not uncommon during the course of outdoor activities that a person may desire to remove the sunglasses for periods of time to avoid their interference with the wearer's vision, but then it is a problem to retain the glasses and have them readily available again for use when desired. This problem of convenience has been previously addressed and resulted in structures which are the subjects of two previously issued patents. These patents are U.S. Pat. No. 4,819,274 issued Apr. 11, 1989 to Shenq Day and U.S. Pat. No. 4,179,753 issued Dec. 25, 1979 to Sue Aronberg. Each of these two patents disclose structures whereby the problem is solved to a certain extent by providing means for storage and carrying of the eyeglasses in a non-operational position with respect to the headgear portion such as a cap or a visor with headband. Such structures have not been found to be fully satisfactory as substantial difficulty is experienced in either placing the glasses in use or returning them to their stored position.

Another patent illustrating a structure directed to this problem of providing association of eyeglasses and a cap structure in attempting to achieve convenience is U.S. Pat. No. 1,133,056 issued Mar. 23, 1915 to Isaac Pachner. Again, this particular structure does not provide the desired degree of convenience in that there is some difficulty associated with moving the eyeglasses from a utilization position to a stored position on the hat. Also, this particular apparatus does not alleviate the problem introduced through physical contact of the eyeglass with the wearer's head, and thus, there is physical strain and discomfort induced in that aspect.

Two other patents that are also directed to this combination type structure of protective eyeglass and headgear are U.S. Pat. No. 1,216,635 issued Feb. 20, 1917 to Earnest Washington and U.S. Pat. No. 1,781,832 issued Nov. 18, 1930 to Erswell Crenshaw. These latter two patents also have the disadvantage of producing physical discomfort in that the eyeglasses are retained against the wearer's face through an elastic band structure, but these structures also have the further disadvantage in that the placement of the eyeglass section in a stored position not only requires removal of the headgear so that the storage can be accomplished, but when so stored, the eyeglass portion is in contact with the wearer's skin or hair and can thus become covered with perspiration or materials that are applied to the person's hair and thereby impair the ability of a person to view objects through the eyeglass.

SUMMARY OF THE INVENTION

In accordance with this invention, headgear is provided which includes a head element that in one embodiment provides protection by blocking the sun rays and in combination therewith an eye shield for filtering or attenuating the light rays that would otherwise be incident to the wearer's eyes. The head element includes a headband section or portion that is adapted to be secured in a removable fashion to the wearer's head and a forehead section carried by the headband and which is adapted to receive and store the lens structure. The combination structure has the eye shield and its associated lens structure mechanically secured to the head element in a manner such that it may be readily pivoted from a stored or nonuse position to an operative position in front of the wearer's eyes. The forehead section provided on the head element defines a storage compartment which is completely separated from the body of the wearer and is thus capable of protecting the lens structure and maintaining the surfaces of the lens in a clean condition.

The eye shield in the combination structure of this invention is pivotally mounted on a head element to enable its selective displacement between a stored position with the lens structure contained within the storage compartment and an operative position. The lens structure is formed with support arms that are pivotally connected to the head element and, through cooperative detent means, may be selectively positioned at the desired relative position between a fully lowered position and positions which are slightly elevated in the direction of the storage compartment. This selective positioning capability not only enhances the versatility of the combination structure to suit or accommodate a person's particular desires at any particular time of wearing, but also has the substantial advantage of having the eye shield supported, if so desired, entirely by the head element and avoid the physically tiresome and uncomfortable contact normally associated with an eyeglass structure resting on the wearer's nose as well as being in engagement with portions of the ears.

Also in accordance with this invention, the eye shield is advantageously mounted on the head element in a manner such that it may be operated without removal of the head element. The person wearing the head element can adjust the eye shield lens structure to a selected position, either stored or operative, through manipulation of support frames that pivotally connect the eye shield to the head element. This pivoting can be readily and easily accomplished through the wearer simply engaging the support frames with the finger tips.

In accordance with this invention, the head element is also advantageously provided with a sun blocking device in the nature of a visor or extended bill structure. Thus, the structure has the combination of a sun blocking visor element to prevent direct contact of the sun's rays with the person's eyes, and an eye shield to attenuate or otherwise modify the lightwaves that are incident to the wearer's eyes.

These and other objects and advantages of this invention will be readily apparent from the following detailed description of an illustrative embodiment thereof and the accompanying drawings.

DESCRIPTION OF THE ILLUSTRATIVE EMBODIMENTS

Figure 1:
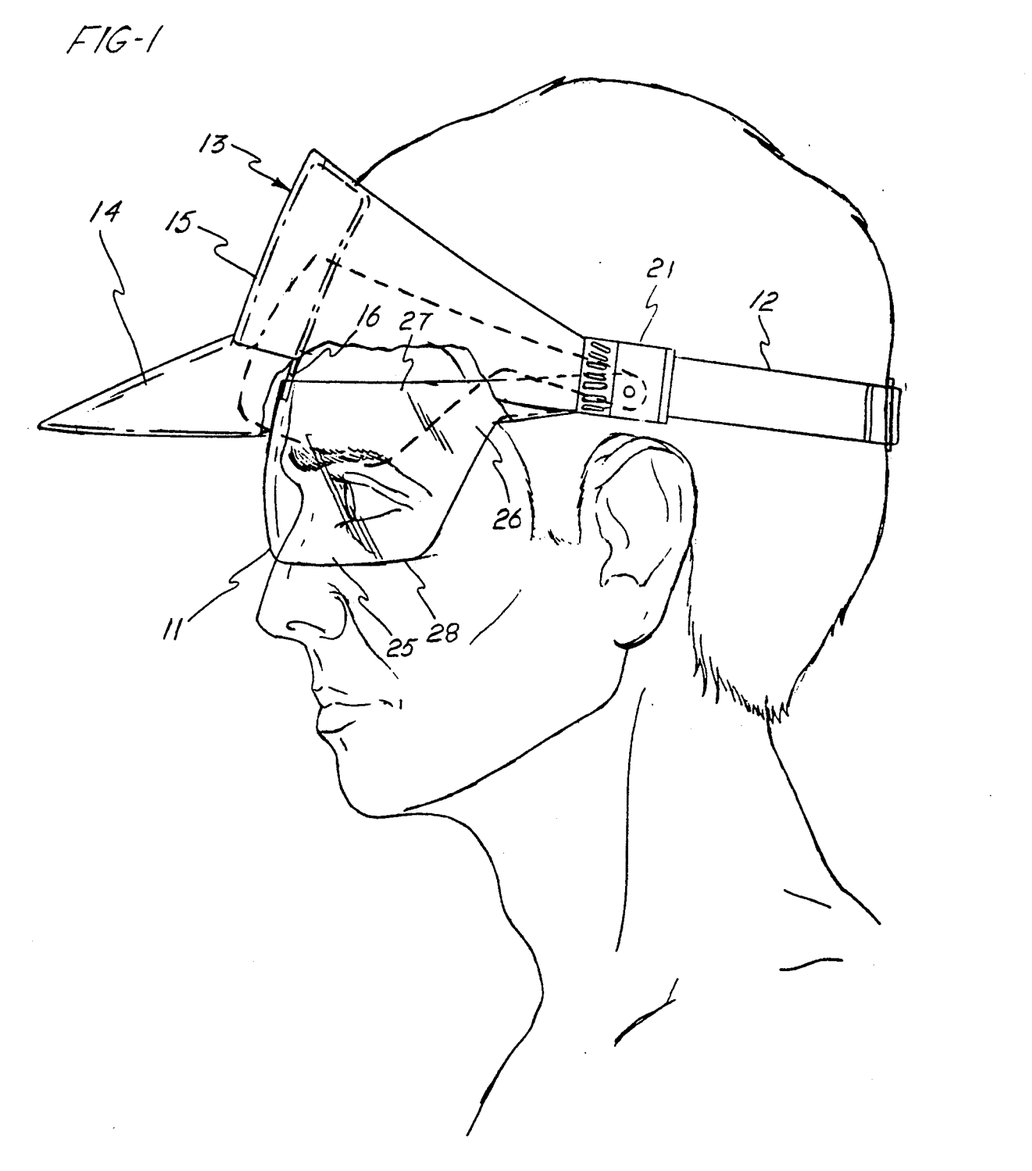
FIG. 1 is a side elevational view of headgear embodying this invention and positioned on a person's head with portions thereof broken away for clarity of illustration.
Figure 4:
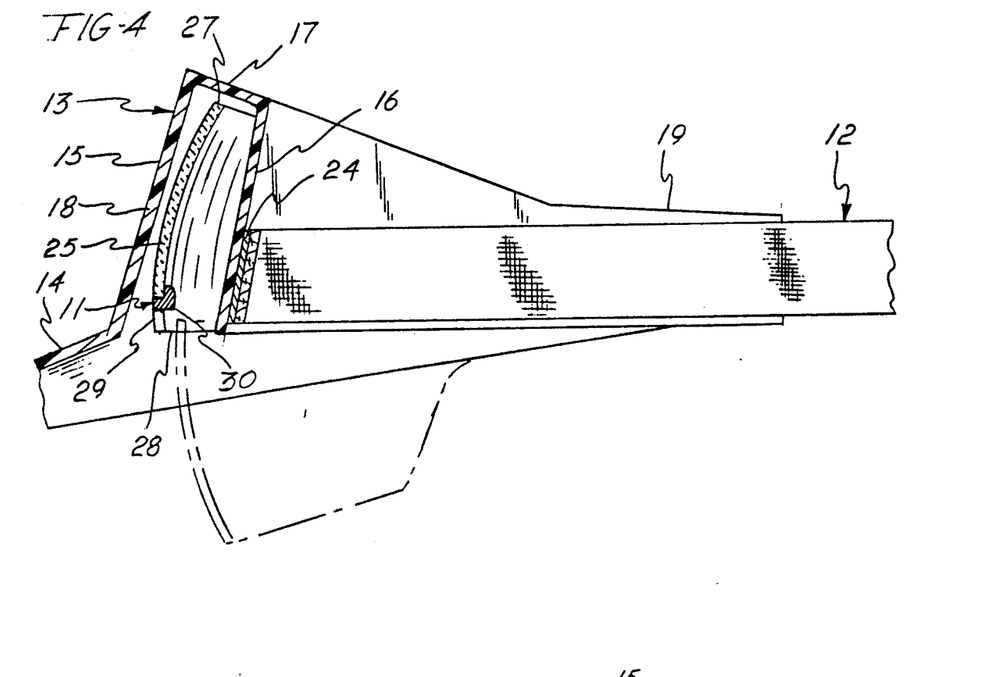
FIG. 4 is a fragmentary sectional view on an enlarged scale taken along line 4—4 of FIG. 2.

Having reference to the drawing figures, headgear embodying this invention is shown in FIG. 1 as positioned on the person's head. The headgear includes the two basic components of a head element designated generally by the numeral 10 and an eye shield designated generally by the numeral 11. The eye shield is shown in FIG. 1 when it is disposed in operative relationship to the person's eyes. The eye shield 11 is shown in FIG. 4 in its stored position. In this illustrative embodiment, the head element is of a type which is commonly described as a visor-type unit in that it includes only a head engaging band 12 and a forehead section 13 provided with a forwardly extending visor 14.

Figure 2:
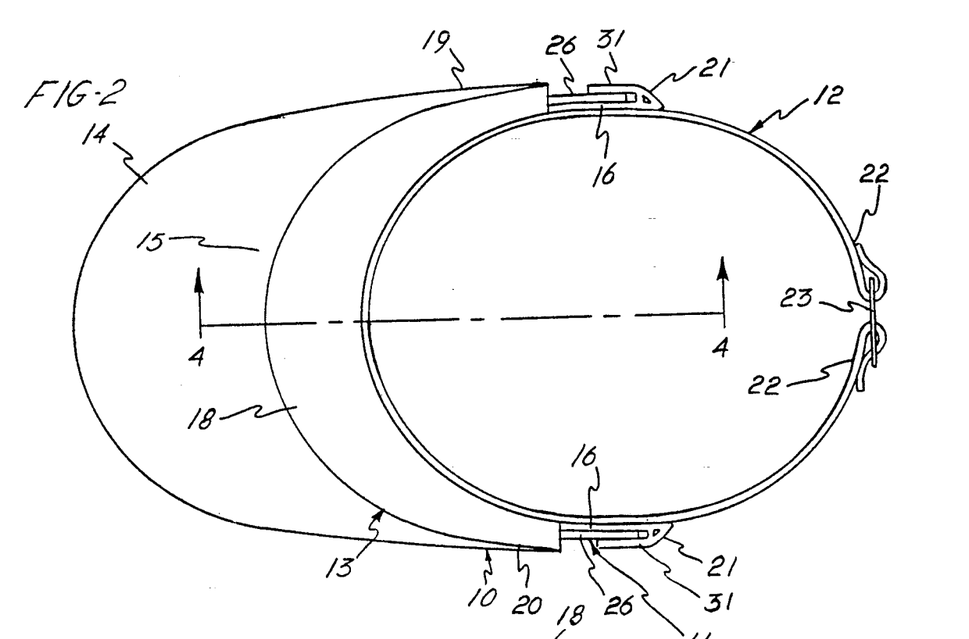
FIG. 2 is a top plan view thereof.
Figure 3:
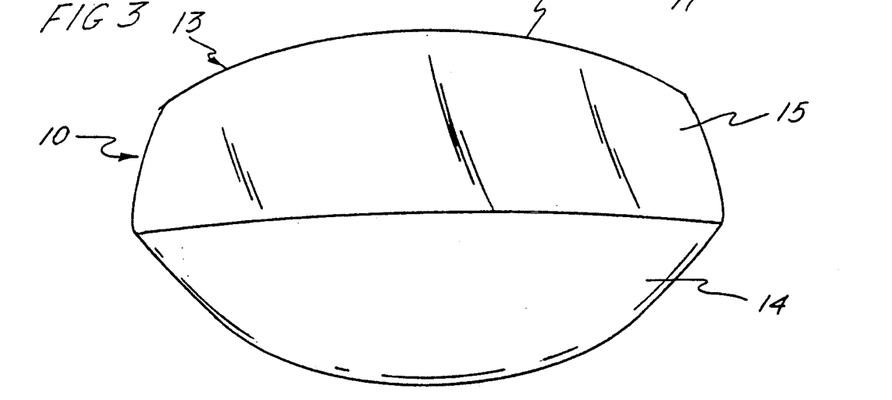
FIG. 3 is a front elevational view thereof.

The forehead section 13 in this illustrative embodiment is fabricated from a suitable plastic material by appropriate molding techniques to form a unitary, substantially rigid structure. It includes spaced apart front and rear walls 15 and 16 that are disposed in generally upstanding relationship when the headgear is placed on the wearer's head and extend across the forehead and a distance rearwardly along the side. These walls 15 and 16 are interconnected at their upper edges by a top wall 17 as can be best seen in FIGS. 2 and 4 with the walls thus defining a cavity or compartment which, as will be subsequently described, is utilized for the storage of the lens structure of the eye shield. The general shape of the forehead section 13 is commensurate with the general forehead shape of a person's head and as can be seen in FIGS. 2 and 4, has a generally semicircular arcuate configuration. With the forehead section 13 designed to be positioned on the forehead of the wearer at a location above the level of the eyes, it has a central forward section 18 that is inclined upwardly and rearwardly to a slight extent to conform to the slope of the general forehead shape. This central section terminates in lateral side sections 19 and 20 that project a distance in a general rearward direction along the sides of the wearer's head. The rear wall 16 continues in each respective lateral side section 19 and 20 a distance further than the front wall 15 to form a support bracket 21 on which the eye shield 11 is mechanically coupled and supported for pivotal movement. The support brackets 21 extend a distance relatively rearward to be positioned at a point which approximates a centrally located position vertically above the wearer's ears.

Figure 6:
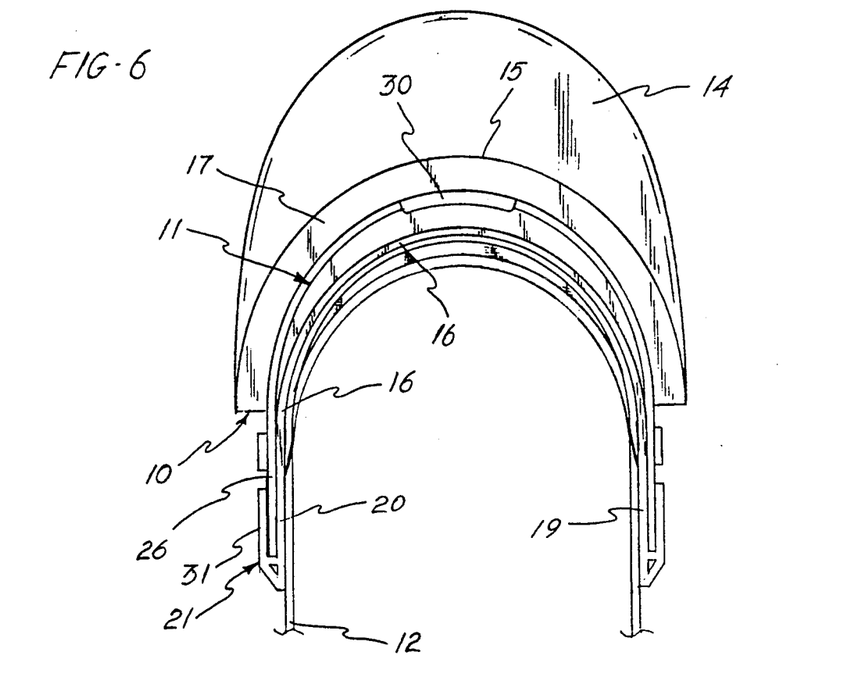
FIG. 6 is a bottom plan view thereof.
Figure 8:
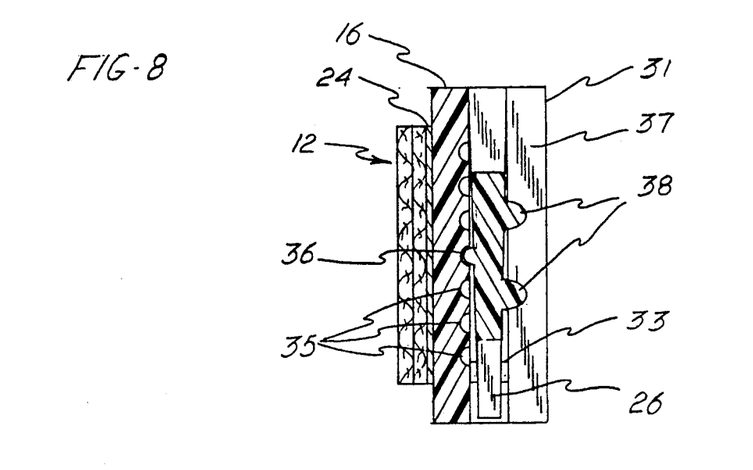
FIG. 8 is a sectional view taken along line 7—7 of FIG. 7.
Figure 9:
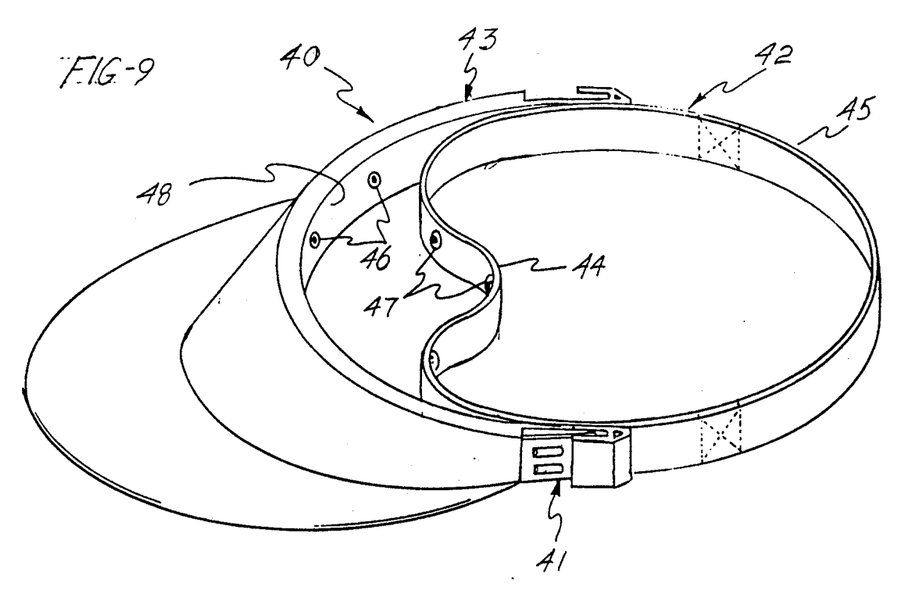
FIG. 9 is a perspective view of a modified headgear embodying this invention.

Securing of the head element 10 in retained relationship on the wearer's head is effected by the head engaging band 12. That band as can be best seen in FIGS. 2, 4 and 6 comprises an elongated strap fabricated from suitable fabric material which is secured to the exposed surface of the rear wall 16 and its associated lateral side sections 19 and 20 terminating in ends 22 adapted to be mechanically coupled at the rear of the wearer's head by a coupling device 23. The band 12 in this embodiment of headgear designed for active outdoor use is advantageously fabricated from a fabric material which exhibits a degree of absorbency for moisture. Such a material makes the headband more comfortable from a wearing standpoint as well as performing the moisture absorbing function highly desired by those persons engaged in strenuous physical activities. However, it will be understood that the band 12 need not be fabricated from such a material where a perspiration problem is not of significant concern. It is also advantageous that the coupling device 23 be of a type which enables the wearer to effect length adjustment to obtain the desired degree of constriction that will maintain the headgear in position, but will not be so tight as to result in discomfort over long term periods of use. The band 12 at its portions which are in association with the rear wall 16 of the forehead section 13 may be securely fixed thereto such as by a suitable adhesive which is diagrammatically illustrated as a layer of adhesive in FIGS. 4 and 8. While the band 12 is shown in this embodiment as being essentially permanently affixed to the forehead section 13, it will be understood that the band may be secured by means which will enable its removal. This is of particular importance in connection with a band which is moisture absorbent and essentially functions as a sweatband to permit its laundering at periodic intervals. Means for releasably securing the band to the forehead section is shown in the embodiment of FIG. 9 where devices as snap fasteners are utilized It will also be understood that the band 12 may include a section which is of elastic construction and replaces a mechanical coupling device 23 such as is shown in the illustrative embodiments. Specific mechanical features of the headband and its securing to the forehead section 13 are matters of design preference and adaptability to specific uses and applications. As such, these specifics are not deemed to be of significance to the invention that is disclosed in this specification and drawings although a specific detachable type band of an elasticized constructions is illustrated in FIG. 9 of the drawings and is subsequently described in detail.

Figure 5:
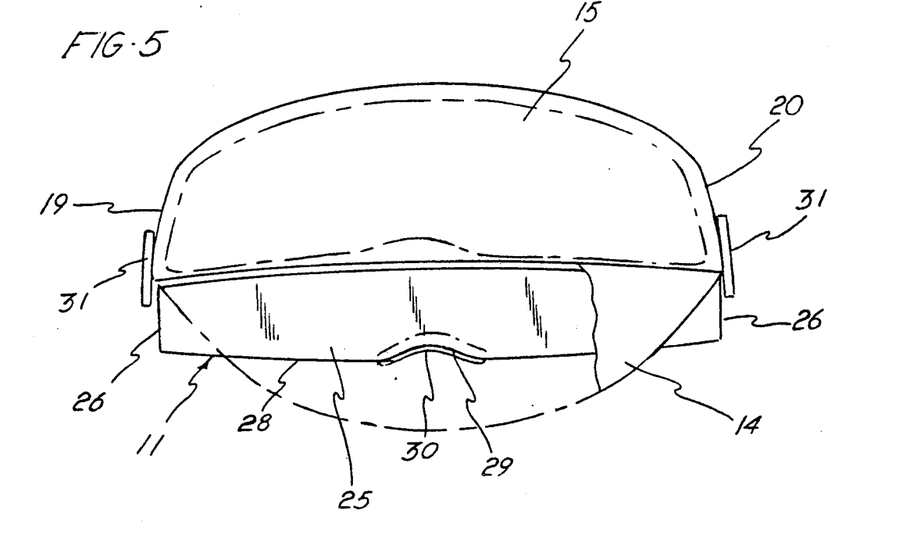
FIG. 5 is a front elevational view similar to FIG. 3, but on an enlarged scale with portions of the visor and other elements removed for clarity of illustration.

The eye shield 11 shown in the illustrative embodiment of this invention is of a unitary construction in what is often referred to as a wraparound style. It includes a lens structure 25 that is adapted to extend across the front of the wearer's eyes and has support means in the form of support arms 26 at each side that are adapted to mechanically intercouple with the respective support brackets 21 at each side of the head element. The lens structure and its support arms are fabricated from a suitable plastic material by appropriate molding techniques to produce a lens structure having a generally continuous planar configuration with a slight curvature in a vertical plane as can be seen in FIG. 1 that extends across the wearer's eyes and is of predetermined extent in vertical dimension to provide sufficient coverage. This lens structure has an upper peripheral edge 27 that is contiguous with the upper peripheral edge of the respective support arms 26. The lens structure has a lower peripheral edge 28 which curves relatively upward at the sides of the central lens structure and continues as the lower edge of the respective support arms 26. This configuration, as can be best seen in FIGS. 1, 4, 5 and 7, results in a relatively narrow support arm which minimizes the material that is required for its fabrication as well as enhancing its aesthetic appearance. Referring to FIG. 5, it will also be seen that the lower peripheral edge 28 of the lens structure is formed at its central area with an upwardly recessed portion 29 to provide adequate clearance as to the upper portions of the wearer's nose. It will also be noted in FIGS. 4 and 5 that this recessed portion 29 is provided with a strip of material 30 formed from a material which provides protective cushioning should the headgear be worn in a manner where the lens structure will be positioned with its lower edge resting on the wearer's nose. The shape of the lens structure 25 and its support arms 26 is designed to generally conform to the cavity formed by the front and rear walls 15 and 16 of the forehead section so as to enable it to interfit within that cavity for storage.

The lens structure is fabricated from a plastic material which is selected because of its characteristics to affect the lightwaves that are intended to be transmitted therethrough. To function as sunglass, this plastic material exhibits the characteristic of at least attenuating lightwaves within the visible spectrum as well as advantageously also attenuating or eliminating lightwaves that may be within the shorter wavelength spectrums such as ultraviolet. It is the ultraviolet and other shorter wavelength lightwaves that are particularly damaging to a person's optical system and thus their elimination or attenuation is particularly advantageous. Lens structures for a device of this nature are not generally designed to provide optical characteristics in the sense of enhancing the visual acuity of the wearer although it is contemplated that the lens structure, if desired, may be so constructed.

Figure 7:
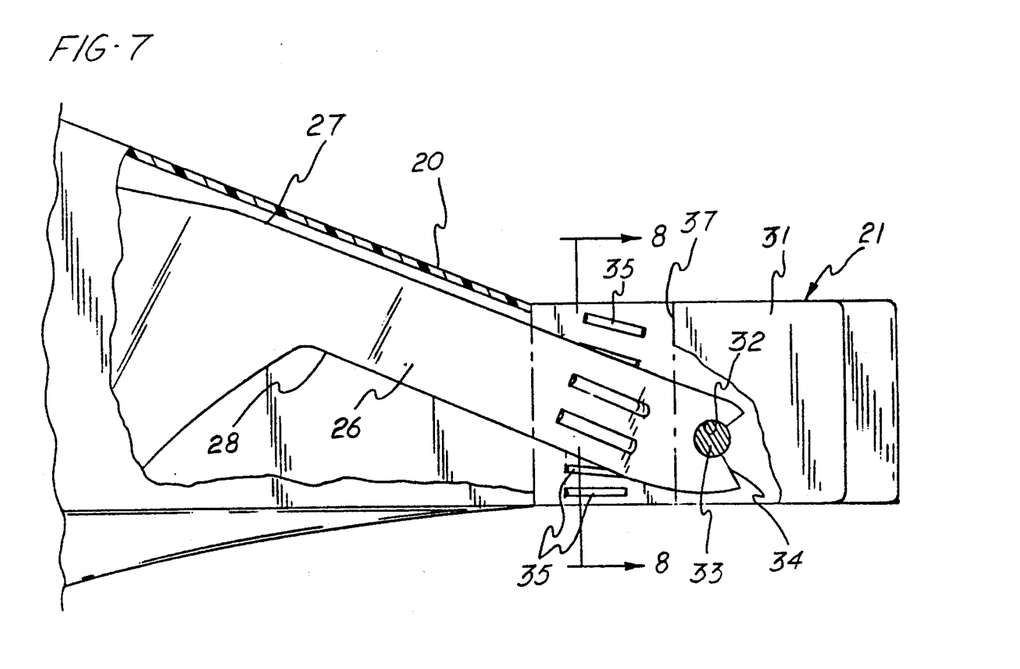
FIG. 7 is a fragmentary side elevational view of the head element and eye shield at their point of interconnection at the side as is shown in FIG. 1, but on a substantially enlarged scale.

The support arms 26 of the eye shield 11 are mechanically coupled with the head element 10 to enable the eye shield to be pivoted in an upward and downward direction as well as to maintain the eye shield in a selected vertical position with respect to the head element. In FIG. 1, the eye shield 11 is shown in a lowered, operative position where the lens structure 25 is disposed in blocking relationship to the wearer's eyes, whereas in FIG. 4, the lens structure is shown elevated to the stored position within the cavity defined by the walls 15 and 16 of the forehead section 13 Specifics of the mechanical structure of the support brackets 21 formed with the lateral side sections 19 and 20 of the forehead section as well as the terminal rear end portions of the support arms 26 can be seen in greater detail in FIGS. 7 and 8. As can be seen, each support bracket 21 includes an outer wall section 31 that is spaced outward from the respective continuation of the lateral side section 19 or 20 a distance sufficient to receive the flat end portion of the respective support arm 26 between the two opposed wall surfaces. In the illustrated construction, this outer wall section 31 is integrally formed with the respective lateral side section 19 or 20 resulting in a unitary structure. As such, the outer wall section 31 extends forwardly from the rearmost end of the lateral side section forming therewith a socket that opens in a forward direction. Each of the support arms 26 is formed with a bearing socket 32 adapted to be journalled on a trunnion or axle 33 that extends transversely between the outer wall section 31 and adjacent lateral side section 19 or 20 and is fixed in those two wall structures. Each of the bearing sockets 32 is formed with a rearwardly opening V-shaped throat 34 which, through the inherent resilience of the plastic material from which the arm is fabricated, enables the throat to expand sufficiently to enable the arm to be snap locked onto the respective axle 33 as is shown in FIG. 7.

Retention of the eye shield 11 in a desired position with respect to the head element 10 is effected through a mechanical detent mechanism. This detent mechanism comprises a series of U-shaped grooves 35 that are molded in the respective lateral side section 19 or 20 and extends generally longitudinally thereof. Formed on the wall of each support arm 26 is a detent ball 36 which projects in an inward direction toward the respective lateral side section 19 or 20 and is designed to interengage with the U-shaped grooves 35 and thereby effect mechanical interlocking. The support arms 26 being fabricated from a plastic material have a certain degree of resilience and this resilience enables the support arm to flex slightly outward as they are pivoted about the respective axles 33 in moving to a selected one of the detent positions. Referring to FIGS. 1 and 2, it will be seen that the outer wall section 31 terminates in a vertical edge 37 a distance rearwardly from the rear terminal end of the front wall 15 of the forehead section 13. This leaves a short space for the purpose of enabling the wearer to insert a finger in engaging with the respective exposed portion of the support arm and effect its displacement in an upward or a downward direction. To facilitate this mechanical engagement of the finger with the support arm, each of the arms includes a pair of finger-grip ribs 38 that project a distance outwardly from the outer face of the support arms. These ribs enable the person to more securely grip the support arm and effect its pivotal displacement by pushing it in an upward or downward direction.

It was previously noted that the headband 12 could be constructed in a manner such that it could be detachably connected to the forehead section 13. An embodiment of headgear illustrating this variation is illustrated in FIG. 9. This structure has a head element 40 and an eye shield 41. The head element includes a head engaging band 42 and a forehead section 43. The forehead section 43 is constructed in substantially the same manner as that illustrated in FIGS. 1–8 as is the eye shield 41. Accordingly, details of the construction of those components in this variant are not otherwise illustrated or described. The headband 42 comprises two sections that are designated as front section 44 and rear section 45. The front section 44 may be formed from a fabric material that is not extensible as that previously described with respect to the first described embodiment and also has a characteristic moisture absorbing capability to function as a sweatband. The rear section 45 which is joined to the front section at each side as by sewing is also fabricated from a material of woven nature, but it incorporates a degree of elasticity. Thus, the headband can readily adapt to the size of a particular person's head with relative ease and also comfort.

In this variation the headband 42 is adapted to be removably connected to the forehead section 43. This is accomplished by mechanical devices such as a plurality of snap fasteners that include the mechanically interlocking socket section 46 and locking pin section 47. The socket sections 46 are secured in a rear wall 48 of the forehead section 43 with the locking pin sections 47 being secured as by sewing to the forwardly facing surface of the front section 44 of the headband. Detachability of the headband from the forehead section facilitates the cleaning of the headband which is of particular importance in the case where the headband is designed to also function as a sweatband. The removability feature of the headband also enables interchange of different size headbands to readily adapt the headgear to different persons as well as enabling the entire headband to be changed should it become deteriorated to the extent that it is no longer suitable for wear.

It will be noted that while the illustrated embodiments of the invention are of a visor-type headgear, the structure may take different configurations, but still retain the advantageous combination of the head element and eye shield as has been described. For example, a forehead section such as that which has been illustrated and described may be incorporated in other headgear designs such as a cap that fully covers a person's head or in a hat or protective helmet-type structure. In such cases, the headband will generally be incorporated as a part of the head covering regardless of its nature and it will not be necessary to provide a headband element such as in the case of the illustrated embodiments. The head covering in such modifications could advantageously cover the forehead section forming the storage compartment if so desired for aesthetic purposes.

It will be readily apparent from the foregoing detailed description of the illustrative embodiments, that a particularly novel and advantageous headgear is provided to protect the wearer from lightwaves. The headgear, being constructed with a head element having an eye shield that is pivotally interconnected therewith, results in the eye shield always being retained with the headgear and quickly and easily available for utilization. Forming a storage compartment or cavity in the head element not only provides a concealed space for the lens structure of the eye shield, but also provides physical protection against inadvertent damage which often occurs in the case of sunglasses that are merely maintained in a carrying case or other receptacle such as shirt pockets and purses. An important advantage of the combination structure of this invention is that the eye shield is convenient to wear and provides significant comfort advantage in that the lens structure need not rest on the wearer's nose and thereby cause discomfort and irritation. Also, the construction enables the wearer to place the headgear in any appropriate selected position on the head to enhance its comfort and usability as to proper location of the lens structure and also in obtaining the shielding effect from the visor.

Having thus described this invention, what is claimed is:

1. Headgear to be worn by a person comprising
   a head element including
      head engaging means for removably securing said head element on a wearer's head,
      a forehead section carried by said head engaging means in a position to extend at least partially across the forehead of a wearer's head and having front and rear spaced apart walls disposed in upstanding relationship when said head element is positioned on a wearer's head and cooperatively defining a storage cavity opening in a downward direction and extending a distance around the front of a wearer's head to at least encompass the horizontal breadth of said front wall, said front and rear spaced apart walls interconnected by a top wall, and an eye shield including
   a lens structure of a configuration to extend across the forward portion of the wearer's face in frontal blocking relationship to the wearer's eyes and selectively positionable within said storage cavity, said lens structure being transmissive of lightwaves within the visible spectrum, and
   support means mechanically coupled with said lens structure and secured to said head element for support of said lens structure, said support means being pivotally operable to enable displacement of said lens structure between a position within the storage cavity of said forehead section, said position always being lower than said top wall, and a functioning position with respect to the wearer's eyes and having position retaining means mechanically interengageable with said head element, and said support means operative to maintain said lens structure in a selected position with respect to said head element.

2. Headgear according to claim 1 wherein said forehead section is of substantially rigid construction.

3. Headgear according to claim 1 wherein said forehead section includes a sheet-form element disposed in relatively forward projecting relationship to the front wall of said forehead section for restricting incidence of lightwaves to the wearer's eyes.

4. Headgear according to claim 3 wherein said forehead section and sheet-form element are molded from plastic material and are of substantially rigid construction.

5. Headgear according to claim 1 wherein said forehead section includes a support bracket carried at each lateral side thereof at a position to be disposed at a respective side of the head of a person wearing the headgear, said support means of said eye shield being mechanically coupled with said support brackets.

6. Headgear according to claim 5 wherein said support means of said eye shield includes a pair of elongated support arms with each arm connected with said lens structure at a respective side thereof, each of said support arms pivotally connected at an end thereof to a respective one of said support brackets for swinging movement in a generally vertical plane for swinging of said lens structure into and out of said storage cavity.

7. Headgear according to claim 6 wherein one of each of said support brackets and support arms is formed with a plurality of sockets and the other is formed with a detent projection operative to mechanically interengage with a selected one of said sockets, said sockets disposed in a vertical array whereby said support arms when pivoted in a vertical plane to a selected position will support and maintain said lens structure in a related position with respect to said forehead section.

8. Headgear according to claim 1 wherein said lens structure is of a generally planar, rectangular configuration.

9. Headgear according to claim 8 wherein said support means of said eye shield includes a pair of elongated support arms, each of said arms being integrally formed with said lens structure at respective opposite ends thereof to extend rearwardly along the sides of the wearer's head.

10. Headgear according to claim 1 wherein said head engaging means includes a band of a length to extend circumferentially around a wearer's head and sized to constrictively engage with the wearer's head at a location above the wearer's eyes and ears.

11. Headgear according to claim 10 wherein said band includes an elasticized portion.

12. Headgear according to claim 10 wherein said band is secured to said forehead section by attachment means operable to selectively permit detachment of said band from said forehead section.

13. Headgear according to claim 6 wherein said support arms and said lens structure are of substantially rigid construction and are rigidly interconnected forming a unitary structure.

14. Headgear according to claim 2 wherein the front and rear walls of said head element's forehead section are rigidly interconnected at their upper ends and are open at each lateral side of said forehead section thereby forming an open-ended, channel-shaped storage cavity.

15. Headgear according to claim 14 wherein said support means includes a pair of elongated, structurally rigid support arms with each arm connected with said lens structure at a respective side thereof, each of said arms having a terminal end portion extending from said cavity at a respective end and pivotally connected to said head element.

16. Headgear according to claim 1 wherein said support means includes a pair of elongated, structurally rigid support arms with each arm connected to said lens structure at a respective side thereof, each of said arms having a terminal end portion extending from a respective end of said storage cavity and pivotally connected to said head element.

17. Headgear according to claim 1 wherein said forehead section includes a support bracket carried at each lateral side thereof, and said support means includes a pair of elongated support arms, each of said support arms being pivotally connected at an end thereof to a respective one of said support brackets, one of each of said support brackets and support arms being formed with a plurality of sockets and the other being formed with a detent projection adapted to mechanically engage with a selected one of said sockets.

18. Headgear according to claim 17 wherein said detent projection projects in an upward direction toward the lateral sides of said forehead section.

19. Headgear according to claim 1 wherein said support means includes a pair of elongated support arms, each of said support arms having formed on its inner wall means for effecting mechanical interlocking of said eyeshield with said head element, and having formed on its outer wall means for gripping said support arm, said means for gripping said support arm projecting a distance outwardly from the outer face of said support arms.

* * * * *